(12) United States Patent
Suzuki et al.

(10) Patent No.: US 10,980,434 B2
(45) Date of Patent: Apr. 20, 2021

(54) PULSEBEAT MEASUREMENT APPARATUS

(71) Applicant: KDDI CORPORATION, Tokyo (JP)

(72) Inventors: Masahiro Suzuki, Fujimino (JP);
Tomoaki Ueda, Tokyo (JP)

(73) Assignee: KDDI CORPORATION, Tokyo (JP)

( * ) Notice: Subject to any disclaimer, the term of this patent is extended or adjusted under 35 U.S.C. 154(b) by 314 days.

(21) Appl. No.: 16/033,115

(22) Filed: Jul. 11, 2018

(65) Prior Publication Data
US 2018/0317791 A1 Nov. 8, 2018

Related U.S. Application Data

(63) Continuation of application No. PCT/JP2016/086009, filed on Dec. 5, 2016.

(30) Foreign Application Priority Data

Jan. 28, 2016 (JP) .............................. JP2016-014096

(51) Int. Cl.
*A61B 5/024* (2006.01)
*A61B 5/0245* (2006.01)
(Continued)

(52) U.S. Cl.
CPC ............ *A61B 5/02444* (2013.01); *A61B 5/01* (2013.01); *A61B 5/0245* (2013.01);
(Continued)

(58) Field of Classification Search
CPC ... A61B 5/02444; A61B 5/01; A61B 5/02055; A61B 5/02416; A61B 5/02438;
(Continued)

(56) References Cited

U.S. PATENT DOCUMENTS 5,018,872 A  5/1991 Suszynski et al.
6,909,271 B2 * 6/2005 Sloneker ................ G01K 7/021
324/117 R
(Continued)

FOREIGN PATENT DOCUMENTS

JP  57-045907 U  3/1982
JP  S57-045907 U  3/1982
(Continued)

OTHER PUBLICATIONS

English Translation of Sugai, Japanese Utility Model Laid-Open No. S57-45907 (Year: 1980).*
(Continued)

*Primary Examiner* — David J. McCrosky
*Assistant Examiner* — Chanel J Jhin
(74) *Attorney, Agent, or Firm* — Fitch, Even, Tabin & Flannery LLP

(57) ABSTRACT

A pulsebeat measurement apparatus includes a first temperature detector configured to detect a temperature of a human body; a second temperature detector, having the same characteristic as that of the first temperature detector, configured to detect a temperature of the human body; a heat accumulator, contacting the second temperature detector, configured to suppress a change in temperature of the second temperature detector; a specifying unit configured to specify a period of a change in temperature caused by a pulsation of the human body based on a difference between the temperature of the human body detected by the first temperature detector and the temperature of the human body detected by the second temperature detector; and a pulsebeat measurement unit configured to measure a pulsebeat based on the specified period of the change in temperature.

8 Claims, 5 Drawing Sheets

(51) Int. Cl.
*A61B 5/00* (2006.01)
*A61B 5/0205* (2006.01)
*A61B 5/01* (2006.01)

(52) U.S. Cl.
CPC ...... *A61B 5/02055* (2013.01); *A61B 5/02438* (2013.01); *A61B 5/681* (2013.01); *A61B 5/6802* (2013.01); *A61B 5/7225* (2013.01); *A61B 5/7278* (2013.01); *A61B 2562/0271* (2013.01)

(58) Field of Classification Search
CPC ..... A61B 5/0245; A61B 5/681; A61B 5/7278; A61B 5/6815; A61B 2562/0271; A61B 2562/04; A61B 2560/0214; A61B 5/441; A61B 5/6804; A61B 2562/18
USPC ........................................................ 600/500
See application file for complete search history.

(56) References Cited

U.S. PATENT DOCUMENTS

| | | |
|---|---|---|
| 9,500,535 B1 | 11/2016 | Urban et al. |
| 2002/0008042 A1 | 1/2002 | Pierro, Jr. et al. |
| 2002/0143257 A1 | 10/2002 | Newman et al. |
| 2003/0171655 A1* | 9/2003 | Newman ............. A61B 5/0059 600/200 |
| 2004/0102914 A1 | 5/2004 | More |
| 2004/0167381 A1 | 8/2004 | Lichter et al. |
| 2005/0152146 A1 | 7/2005 | Owen et al. |
| 2007/0295713 A1* | 12/2007 | Carlton-Foss ........... A61B 5/01 219/497 |
| 2010/0062683 A1 | 3/2010 | Brundage |
| 2015/0126896 A1 | 5/2015 | AlHazme |
| 2016/0183794 A1 | 6/2016 | Gannon et al. |
| 2016/0262694 A1 | 9/2016 | Calcano et al. |
| 2016/0310112 A1 | 10/2016 | Gevaert et al. |
| 2018/0263508 A1 | 9/2018 | Yoshihiko et al. |

FOREIGN PATENT DOCUMENTS

| | | |
|---|---|---|
| JP | H04-501611 A | 3/1992 |
| JP | H08-266491 A | 10/1996 |
| JP | 2001-000422 A | 1/2001 |
| JP | 2004-528085 A | 9/2004 |
| JP | 2005-519666 A | 7/2005 |
| JP | 2006-102161 A | 4/2006 |
| JP | 3819877 B2 | 9/2006 |
| JP | 2008-245943 A | 10/2008 |
| JP | 2009-279076 A | 12/2009 |
| JP | 2010-264095 A | 11/2010 |
| JP | 2011-133300 A | 7/2011 |
| JP | 2014-139585 A | 7/2014 |
| WO | 2007-138699 A1 | 12/2007 |
| WO | 2014157138 A1 | 10/2014 |
| WO | 2016111261 A1 | 7/2016 |

OTHER PUBLICATIONS

James Philip, "Continuous Thermal Measurement of Cardiac Output", Mary 1984, IEEE Transactions on Biomedical Engineering, vol. BME-31, No. 5 (Year: 1984).*

JPO; Application No. 2016-012254; Office Action dated Feb. 26, 2019.

"Regarding Development and Practical Use of "hitoe" Which Is a Functional Material That Enable Biometric Information to Be Continuous Measured Just by Wearing It", Internet [URL: https://www.nttdocomo.co.jp/info/news_release/2014/01/30_00.html], <search on Jun. 5, 2015>.

Japan Patent Office, International application No. PCT/ JP2016/086009, International Search Report dated Feb. 3, 2017.

* cited by examiner

PULSEBEAT MEASUREMENT APPARATUS

This application is a continuation of international Patent Application No. PCT/JP2016/086009 filed on Dec. 5, 2016, and claims priority to Japanese Patent Application No. 2016-014096 filed on Jan. 28, 2016, the entire content of both of which is incorporated herein by reference.

TECHNICAL FIELD

The present invention relates to a pulsebeat measurement apparatus.

BACKGROUND ART

In recent years, a computer (so-called wearable device) such as a wristwatch, ring, or a pair of glasses which can be directly worn and carried by the user is attracting attention. There is no big difference between simply wearing and carrying a small computer. Therefore, an application technique which makes the best use of a feature of always wearing is required for the wearable device. As such application technique, a vital signs sensing technique of automatically recording the condition of the user at the time of wearing is plausible. An example of the vital signs sensing technique is pulsebeat measurement.

In general, as pulsebeat measurement, electrocardiography of detecting a heart rate almost equivalent to a pulse rate using the peaks, for example, P waves, R waves, or the like of an electrocardiographic waveform measured by attaching electrodes to a living body, photoplethysmography of irradiating a peripheral blood vessel such as a wrist, finger, or earlobe with light, and detecting a pulsebeat based on an optical change in which reflected light periodically changes due to a blood flow and light absorption characteristic, and the like have been widely used.

NPL 1 discloses an apparatus capable of performing heart beat measurement by embedding, in clothing, a measurement electrode according to a sport electrocardiographic lead system, and wearing it. Furthermore, PTL 1 discloses an arrangement capable of measuring a heart beat by wearing, on a pinna, an apparatus including a sensor for performing irradiation with an infrared ray.

CITATION LIST

Patent Literature

PTL 1: Japanese Patent Laid-Open No. 2006-102161

Non Patent Literature

NPL 1: "Regarding Development and Practical Use of "hitoe" Which Is a Functional Material That Enable Biometric Information to Be Continuous Measured Just by Wearing It", Internet [URL: https://www.nttdocomo.co.jp/info/news_release/2014/01/30_00.html], <search on Jun. 5, 2015>

SUMMARY OF INVENTION

Technical Problem

The apparatus disclosed in NPL 1 (electrocardiography) can measure a heart beat correctly since the electrode is worn on the body surface. Since, however, it is necessary to bring the electrode into tight contact with the human body, he/she has an unwell feeling such as a restraint feeling or oppressive feeling. In addition, it is necessary to wash the clothing, and the washing count is limited in terms of durability, thereby impairing the usability.

In the apparatus disclosed in PTL 1, the power consumption of a light emitting element is large. Therefore, for example, if the apparatus is used for a small terminal apparatus such as a wearable device, it is impossible to continuously measure a pulsebeat all the time. In addition, if the user has a tattoo or the like, a coloring matter blocks light, and thus it may be impossible to capture reflected light appropriately.

To solve the above problems, the present inventors propose a wearable pulsebeat measurement apparatus that measures a pulsebeat by specifying occurrence of an instantaneous small change in body temperature of a human body caused by a pulsation in addition to a gradual change in body temperature in daily life, and detecting a small change in temperature caused by a pulsation using a temperature sensor that detects the temperature on a contact surface with the human body. Since, for example, it is only necessary to cause the temperature sensor to contact a wrist, an ankle, or the like, and very low power is required to detect the temperature, the pulsebeat measurement apparatus can be downsized and a pulsebeat can be measured at low power.

However, since a small change in body temperature caused by a pulsation is smaller than noise detected by the temperature sensor together with the temperature, it is necessary to separate the small change in body temperature from the noise.

Solution to Problem

According to an aspect of the present invention, a pulsebeat measurement apparatus includes a first temperature detector configured to detect a temperature of a human body; a second temperature detector, having the same characteristic as that of the first temperature detector, configured to detect a temperature of the human body; a heat accumulator, contacting the second temperature detector, configured to suppress a change in temperature of the second temperature detector; a specifying unit configured to specify a period of a change in temperature caused by a pulsation of the human body based on a difference between the temperature of the human body detected by the first temperature detector and the temperature of the human body detected by the second temperature detector; and a pulsebeat measurement unit configured to measure a pulsebeat based on the specified period of the change in temperature.

Other features and advantages of the present invention will be apparent from the following description taken in conjunction with the accompanying drawings. Note that the same reference numerals denote the same or like components throughout the accompanying drawings.

DESCRIPTION OF EMBODIMENTS

First Embodiment

Figure 1:
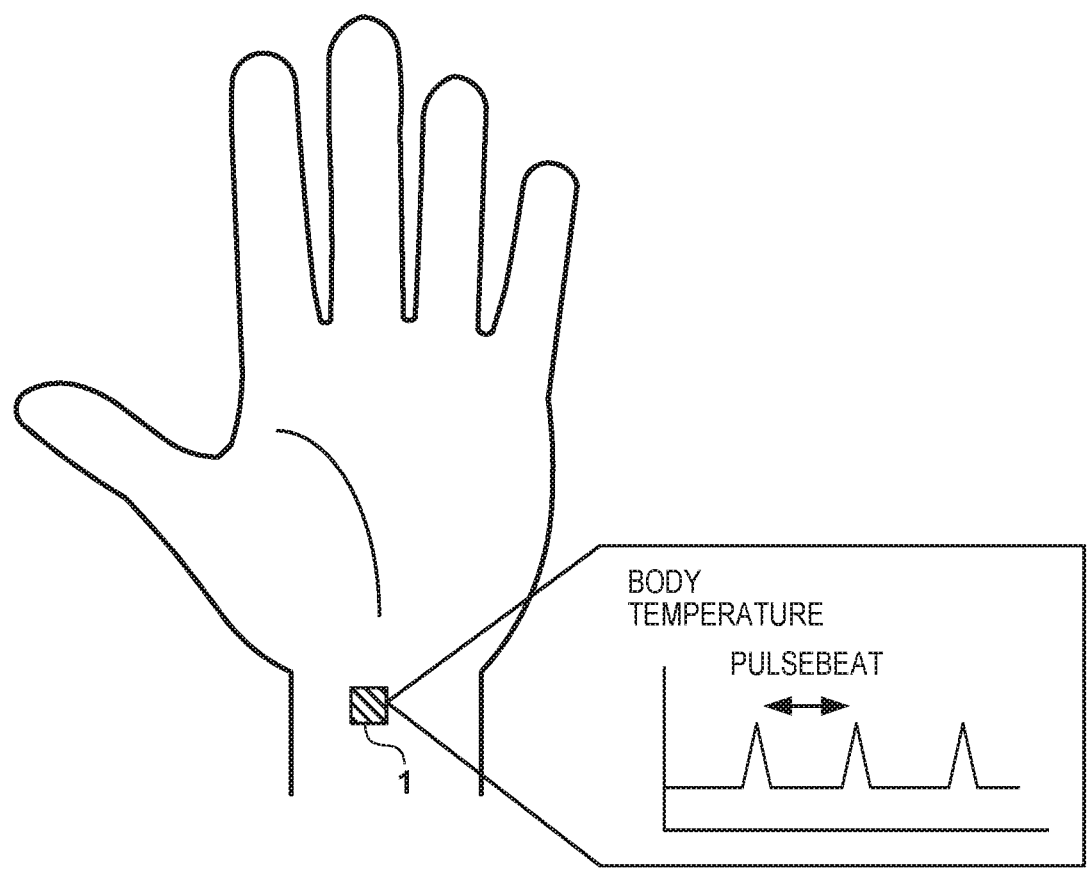
FIG. 1 is a view for explaining a pulsebeat measurement method by a pulsebeat measurement apparatus.

An outline of a pulsebeat measurement apparatus 1 according to this embodiment will be described first with reference to FIG. 1. FIG. 1 is a view for explaining a pulsebeat measurement method by the pulsebeat measurement apparatus 1 according to this embodiment. As shown in FIG. 1, the pulsebeat measurement apparatus 1 detects a small change in body temperature in an arbitrary portion (for example, a wrist, neck, ankle, or the like) of a human body, and measures a pulsebeat based on the period of the small change in body temperature. For example, by providing the pulsebeat measurement apparatus 1 in each of various wearable devices such as a wristwatch type device and a spectacle type device, it is possible to measure the pulse rate of the user wearing the wearable device.

Figure 2:
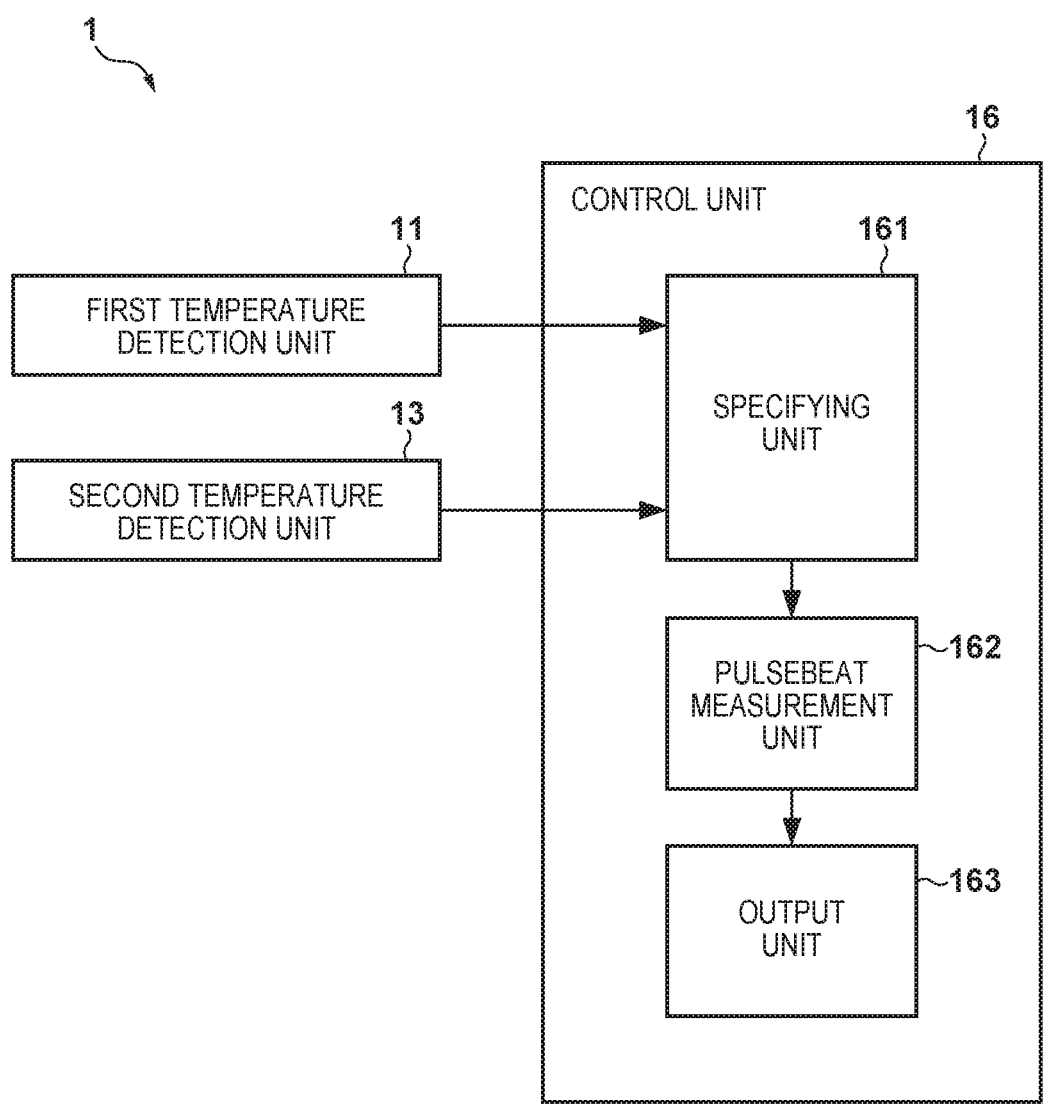
FIG. 2 is a block diagram showing the arrangement of the pulsebeat measurement apparatus according to an embodiment.

FIG. 2 is a block diagram showing the arrangement of the pulsebeat measurement apparatus 1 according to this embodiment. As shown in FIG. 2, the pulsebeat measurement apparatus 1 includes a first temperature detection unit 11, a second temperature detection unit 13, and a control unit 16.

The first temperature detection unit 11 includes, for example, a resistance temperature detector, such as a thermistor-type resistance temperature detector or platinum resistance temperature detector, whose resistance value changes in accordance with a change in temperature, and a lead wire for causing a current to flow into the resistance temperature detector. The first temperature detection unit 11 detects the temperature of a contacting human body. The first temperature detection unit 11 has, for example, a rectangular shape with one side of about 1 mm to 2 mm, and consumes only a small current (for example, several mA or less) to measure a resistance value.

Figure 3:
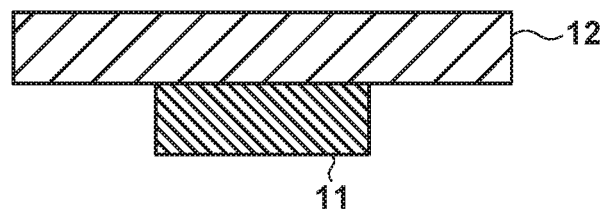
FIG. 3 is a view showing the positional relationship between a first temperature detection unit and a heat dissipation unit according to an embodiment.

The first temperature detection unit 11 contacts a heat dissipation unit 12. FIG. 3 is a view showing the positional relationship between the first temperature detection unit 11 and the heat dissipation unit 12. As shown in FIG. 3, the first temperature detection unit 11 and the heat dissipation unit 12 are stacked.

The heat dissipation unit 12 is, for example, a metal plate. The heat dissipation unit 12 dissipates heat accumulated in the first temperature detection unit 11. Note that if the pulsebeat measurement apparatus 1 is provided in a wearable device, a component with high heat conductivity used in the wearable device may be used as the heat dissipation unit 12.

Since the first temperature detection unit 11 contacts the heat dissipation unit 12, it can dissipate, via the heat dissipation unit 12, heat accumulated in itself. This suppresses the first temperature detection unit 11 from entering the thermal equilibrium state, thereby making it possible to detect a change in temperature of the human body caused by a pulsation all the time.

The second temperature detection unit 13 has the same characteristic as that of the first temperature detection unit 11, and includes a resistance temperature detector, such as a thermistor-type resistance temperature detector or platinum resistance temperature detector, whose resistance value changes in accordance with a change in temperature, and a lead wire for causing a current to flow into the resistance temperature detector, similarly to the first temperature detection unit 11. The second temperature detection unit 13 is arranged near the first temperature detection unit 11. For example, the second temperature detection unit 13 is arranged at a position where the human body can contact the second temperature detection unit 13 simultaneously with the first temperature detection unit 11. The second temperature detection unit 13 detects the temperature of the human body contacting itself. The second temperature detection unit 13 has, for example, a rectangular shape with one side of about 1 mm to 2 mm, and consumes only a small current (for example, several mA or less) to measure a resistance value.

Figure 4A:
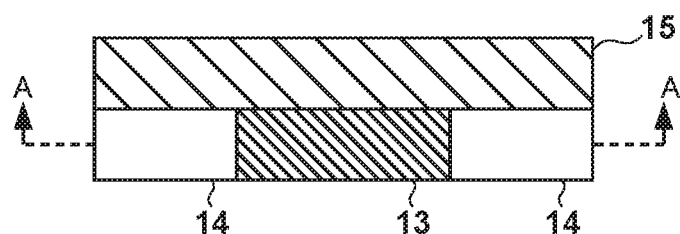
FIG. 4A is a view showing the positional relationship among a second temperature detection unit, a heat accumulation unit, and a heat insulation unit according to an embodiment.
Figure 4B:
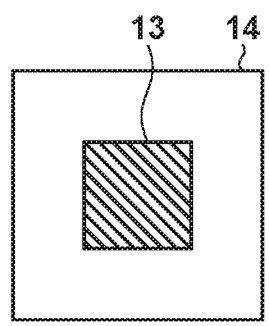
FIG. 4B is a view showing the positional relationship among the second temperature detection unit, the heat accumulation unit, and the heat insulation unit according to an embodiment.

The second temperature detection unit 13 contacts a heat accumulation unit 14 and a heat insulation unit 15. FIGS. 4A and 4B are views each showing the positional relationship among the second temperature detection unit 13, the heat accumulation unit 14, and the heat insulation unit 15. FIG. 4A is a side view showing the second temperature detection unit 13, the heat accumulation unit 14, and the heat insulation unit 15. FIG. 4B is a schematic sectional view taken along a line A-A and showing the second temperature detection unit 13 and the heat accumulation unit 14.

As shown in FIG. 4A, it can be confirmed that the second temperature detection unit 13 and the heat insulation unit 15 are stacked. As shown in FIGS. 4A and 4B, the heat accumulation unit 14 is arranged to surround the second temperature detection unit 13 in a direction orthogonal to the stacking direction of the second temperature detection unit 13 and the heat insulation unit 15.

The heat accumulation unit 14 is made of, for example, a resin or glass. The heat accumulation unit 14 contacts the second temperature detection unit 13 to accumulate heat dissipated from the second temperature detection unit 13, thereby suppressing a change in temperature of the second temperature detection unit 13. Note that the heat accumulation unit 14 is made of a resin or glass but is not limited to this. For example, by mixing a metal in the resin or glass forming the heat accumulation unit 14, heat dissipated from the second temperature detection unit 13 may be distributed to the overall heat accumulation unit 14. This can cause the heat accumulation unit 14 and the second temperature detection unit 13 to transit to the thermal equilibrium state immediately. This can disable the second temperature detection unit 13 to detect a change in temperature of the human body caused by a pulsation.

Figure 5:
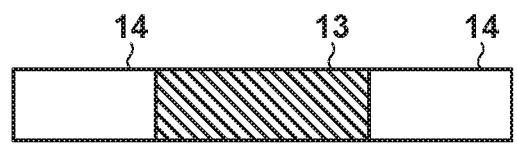
FIG. 5 is a view showing an example in which no heat insulation unit is provided.

The heat insulation unit 15 contacts the second temperature detection unit 13 to suppress heat dissipation from the second temperature detection unit 13. This allows the pulsebeat measurement apparatus 1 to suppress heat from being dissipated from the second temperature detection unit 13, and suppress the second temperature detection unit 13 from changing from the thermal equilibrium state to a state in which heat is transferred. Note that as shown in FIG. 5, the pulsebeat measurement apparatus 1 may not include the heat insulation unit 15 but only the heat accumulation unit 14 arranged on the side surface of the second temperature detection unit 13.

The control unit 16 is formed by, for example, an electric circuit, and measures the pulsebeat of the human body. The control unit 16 includes a specifying unit 161, a pulsebeat measurement unit 162, and an output unit 163. The specifying unit 161 specifies the period of a change in temperature caused by a pulsation of the human body based on the difference between the temperature of the human body detected by the first temperature detection unit 11 and that detected by the second temperature detection unit 13. The specifying unit 161 specifies the period of a change in temperature caused by a pulsation of the human body by performing the following processing.

First, the specifying unit 161 causes a current to flow into the first temperature detection unit 11, and measures a voltage (analog value) applied to the first temperature detection unit 11, thereby measuring the temperature of the human body. Since the heat dissipation unit 12 contacts the first temperature detection unit 11, and the first temperature detection unit 11 is suppressed from entering the thermal equilibrium state, the resistance value of the first temperature detection unit 11 changes in accordance with a change in body temperature caused by a pulsation of the contacting human body. Therefore, the specifying unit 161 can measure the body temperature of the human body reflecting the change in temperature caused by a pulsation by measuring the voltage applied to the first temperature detection unit 11.

The specifying unit 161 causes a current to flow into the second temperature detection unit 13, and measures a voltage value (analog value) applied to the second temperature detection unit 13, thereby measuring the temperature of the human body. Since the heat accumulation unit 14 and the heat insulation unit 15 contact the second temperature detection unit 13, and the second temperature detection unit 13 transits to the thermal equilibrium state immediately, the resistance value of the second temperature detection unit 13 does not change in accordance with a change in temperature caused by a pulsation of the contacting human body. Therefore, the specifying unit 161 can measure the body temperature of the human body not reflecting a change in temperature caused by a pulsation by measuring the voltage applied to the second temperature detection unit 13.

Subsequently, the specifying unit 161 acquires a value corresponding to the difference between the temperature detected by the first temperature detection unit 11 and that detected by the second temperature detection unit 13 by acquiring the difference between the voltage applied to the first temperature detection unit 11 and that applied to the second temperature detection unit 13. The voltage applied to the first temperature detection unit 11 corresponds to the body temperature reflecting a change in temperature caused by a pulsation, and includes noise. The voltage applied to the second temperature detection unit 13 corresponds to the body temperature not reflecting a change in temperature caused by a pulsation and includes noise. Since the second temperature detection unit 13 is arranged near the first temperature detection unit 11, the noise components included in the voltages have the same trend. Therefore, the specifying unit 161 can extract a value indicating only a change in temperature caused by a pulsebeat, from which the noise has been removed, by acquiring the difference between the voltage applied to the first temperature detection unit 11 and that applied to the second temperature detection unit 13.

For example, the specifying unit 161 converts the acquired difference into a digital value by sampling the acquired difference at a predetermined sampling frequency. Although a pulse period obtained from a pulse wave is several Hz, a band higher (for example, about 100 Hz) than the pulse period is required to detect a peak necessary for calculation of a pulse rate. Therefore, by setting a relatively high frequency (for example, 800 Hz) as a sampling frequency, the specifying unit 161 can function as a low-pass filter at the time of conversion into a digital value, and remove high-frequency noise included in the acquired difference.

Note that before converting the acquired difference into a digital value, the specifying unit 161 may acquire a difference by attenuating a signal of a predetermined frequency or higher through the low-pass filter. Then, the specifying unit 161 may convert, into a digital value, the difference obtained through the low-pass filter.

Subsequently, the specifying unit 161 specifies the period of a change in temperature caused by a pulsation of the human body based on the difference converted into the digital value. For example, if the first temperature detection unit 11 has a characteristic that the resistance value (voltage value) decreases along with a rise in temperature, the specifying unit 161 specifies a timing at which the body temperature becomes highest in accordance with a pulsation, by specifying a timing at which the acquired difference becomes low instantaneously. The specifying unit 161 specifies the period of a change in temperature caused by a pulsation of the human body by specifying the period of the timing.

Note that the specifying unit 161 may calculate the moving average of differences converted into digital values during a predetermined period and specify the period of a change in temperature caused by a pulsation of the human body based on the moving average of the differences. With this operation, even if periodic noise remains in the difference, the pulsebeat measurement apparatus 1 can remove the noise and specify the period of a change in temperature accurately. Note that the specifying unit 161 may remove the noise from the difference by approximating the waveform of differences converted into digital values during a predetermined period to a parabola, or applying a rectangular wave correlation filter that correlates the difference and a rectangular pulse formed from positive and negative pulse waves. The specifying unit 161 removes noise by the above-described method. However, the present invention is not limited to this. Noise may be removed by using another noise removal method or combining a plurality of noise removal methods.

The pulsebeat measurement unit 162 measures the pulsebeat of the human body from the period of a change in temperature caused by the pulsation specified by the specifying unit 161. More specifically, the pulsebeat measurement unit 162 considers, as an R-R interval, the period of the change in temperature caused by the pulsation specified by the specifying unit 161, and calculates a pulse rate based on the R-R interval, thereby measuring the pulsebeat of the human body.

The output unit 163 outputs the pulse rate measured by the pulsebeat measurement unit 162. The output unit 163 outputs the measured pulse rate to, for example, the wearable device or the like provided with the pulsebeat measurement apparatus 1. Thus, the wearable device or the like provided with the pulsebeat measurement apparatus 1 can display the pulse rate on a display unit provided in itself, cause a printer to print information including the pulse rate, and transmit information including the pulse rate to an external device.

As described above, the pulsebeat measurement apparatus 1 according to this embodiment specifies the period of a change in temperature caused by a pulsation of the human body based on the difference between the voltage value corresponding to the temperature of the human body detected by the first temperature detection unit 11 and that corresponding to the temperature of the human body detected by the second temperature detection unit 13 on which a change in temperature is suppressed by the heat accumulation unit 14, and measures a pulsebeat based on the specified period of the change in temperature.

Since the voltage value corresponding to the temperature detected by the first temperature detection unit 11 and that corresponding to the temperature detected by the second temperature detection unit 13 include the similar noise, the pulsebeat measurement apparatus 1 can separate a small change in body temperature from noise by acquiring the difference, thereby extracting a value indicating only a change in temperature caused by a pulsebeat. Therefore, the pulsebeat measurement apparatus 1 can specify the period of a change in temperature caused by a pulsation of the human body accurately, and measure a pulsebeat accurately based on the specified period of the change in temperature.

Second Embodiment

A pulsebeat measurement apparatus 1 according to the second embodiment will be described. The pulsebeat measurement apparatus 1 according to the second embodiment is different from the first embodiment in that a heat absorption unit 17 is provided between a first temperature detection unit 11 and a heat dissipation unit 12. The remaining points are the same as in the first embodiment. The difference from the first embodiment will be described below. A description of the same points as in the first embodiment will be omitted appropriately.

Figure 6:
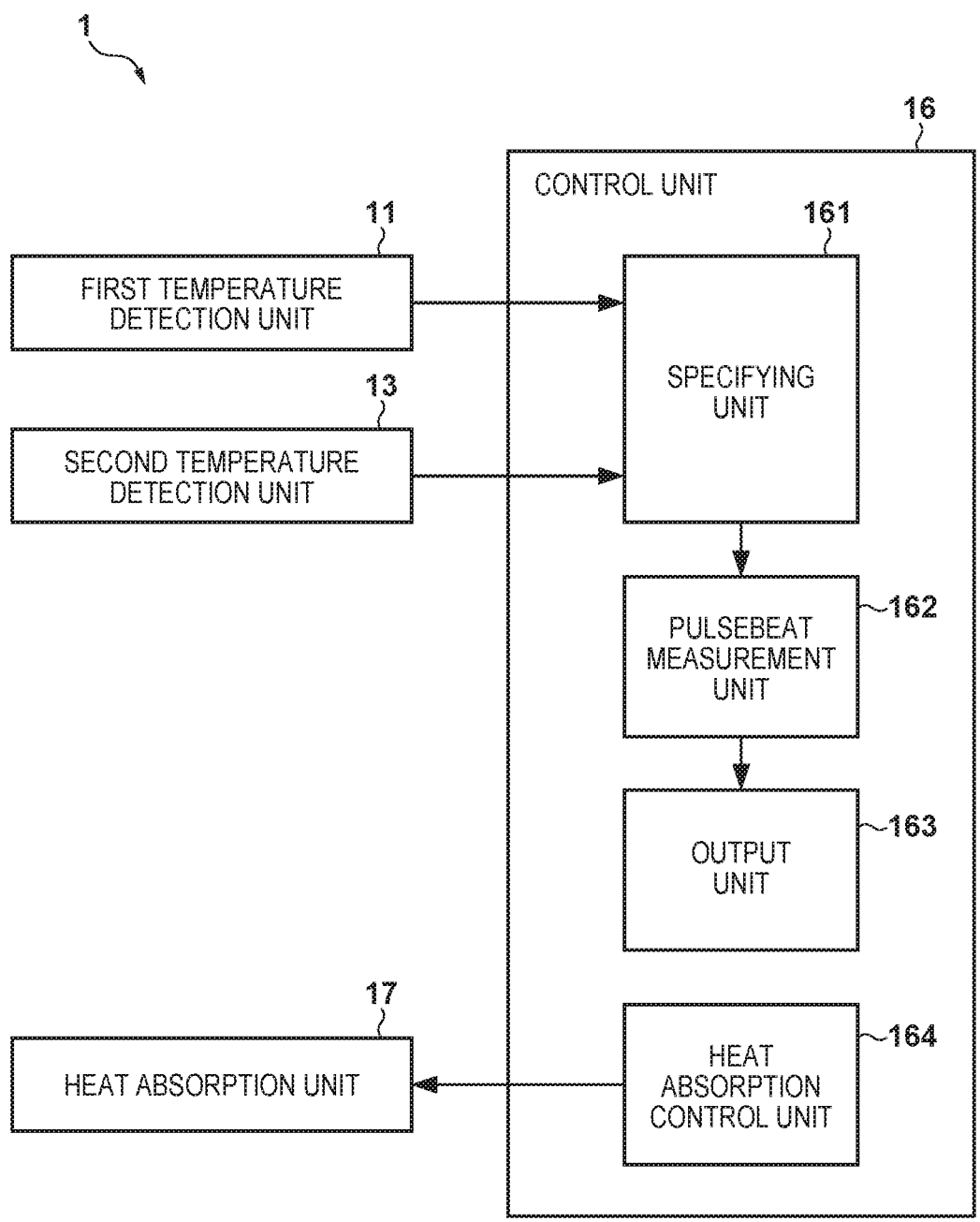
FIG. 6 is a block diagram showing the arrangement of a pulsebeat measurement apparatus according to an embodiment.
Figure 7:
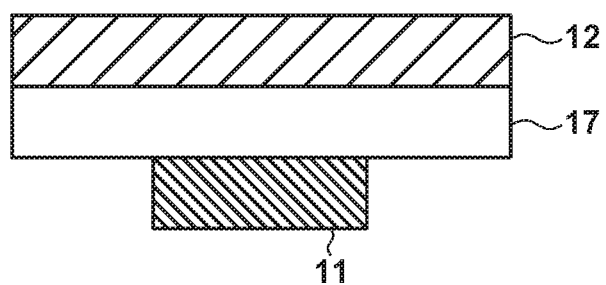
FIG. 7 is a view showing the positional relationship among a first temperature detection unit, a heat dissipation unit, and a heat absorption unit according to an embodiment.

FIG. 6 is a block diagram showing the arrangement of the pulsebeat measurement apparatus 1 according to this embodiment. FIG. 7 is a view showing the positional relationship among the first temperature detection unit 11, the heart dissipation unit 12, and the heat absorption unit 17 according to this embodiment. As shown in FIG. 6, the pulsebeat measurement apparatus 1 further includes the heat absorption unit 17. In addition, a control unit 16 further includes a heat absorption control unit 164.

The heat absorption unit 17 includes, for example, a Peltier device, and has a rectangular shape with one side of about 1 mm to 2 mm. The heat absorption unit 17 includes a heat absorption surface that absorbs heat and a heat dissipation surface that is a surface on the opposite side of the heat absorption surface and dissipates heat absorbed by the heat absorption surface.

As shown in FIG. 7, the first temperature detection unit 11, the heat dissipation unit 12, and the heat absorption unit 17 are stacked. The heat absorption surface of the heat absorption unit 17 contacts the first temperature detection unit 11, and the heat dissipation surface of the heat absorption unit 17 contacts the heat dissipation unit 12. When a heat absorption control unit 164 (to be described later) controls a current flowing into the heat absorption unit 17, the heat absorption unit 17 absorbs heat accumulated in the first temperature detection unit 11 to decrease the temperature of the first temperature detection unit 11. Note that the heat absorption unit 17 consumes only a small current for heat absorption.

Note that in this embodiment, the heat dissipation unit 12 is made to contact the heat absorption unit 17 as a Peltier device, and to dissipate heat absorbed by the heat absorption unit 17 from the first temperature detection unit 11. However, the present invention is not limited to this. For example, a cooling fan may be used as the heat absorption unit 17, instead of the Peltier device. In this case, the first temperature detection unit 11 may be made to contact the heat dissipation unit 12, and the cooling fan may dissipate heat from the heat dissipation unit 12.

The pulsebeat measurement apparatus 1 may further include a heat insulation unit that suppresses transfer of heat between a human body and the heat absorption unit 17. The heat insulation unit may be arranged to surround the first temperature detection unit 11 in a direction orthogonal to the stacking direction of the first temperature detection unit 11 and the heat absorption unit 17. Thus, since the first temperature detection unit 11 and the heat insulation unit exist between the human body and the heat absorption unit 17, it is possible to prevent the human body from contacting the heat absorption unit 17.

The heat absorption control unit 164 controls cooling of the first temperature detection unit 11 by controlling a current flowing into the heat absorption unit 17. For example, the heat absorption control unit 164 cools the first temperature detection unit 11 by causing a constant current to flow into the heat absorption unit 17 all the time.

Note that the pulsebeat measurement apparatus 1 may include a third temperature detection unit that detects the temperature on the heat absorption surface or heat dissipation surface of the heat absorption unit 17, and the heat absorption control unit 164 may control, based on the difference between the temperature detected by the first temperature detection unit 11 and that detected by the third temperature detection unit, a current flowing into the heat absorption unit 17 so that the temperature of the first temperature detection unit 11 becomes lower than the temperature of the human body by a predetermined temperature (for example, 3°).

The heat absorption control unit 164 may cause a current to intermittently flow into the heat absorption unit 17 in accordance with the period of a pulsebeat specified by a specifying unit 161. This can reduce power required to control cooling of the first temperature detection unit 11.

As described above, the pulsebeat measurement apparatus 1 according to this embodiment further includes the heat absorption unit 17 that absorbs heat of the first temperature detection unit 11. With this arrangement, the heat absorption unit 17 absorbs heat accumulated in the first temperature detection unit 11 to cool the first temperature detection unit 11. Therefore, it is possible to further suppress the first temperature detection unit 11 from entering the thermal equilibrium state and accurately detect a change in temperature of the human body caused by a pulsation, as compared to a case in which only the heat dissipation unit 12 is provided.

Furthermore, by configuring the heat absorption unit 17 to include a Peltier device, the pulsebeat measurement apparatus 1 forcibly absorbs heat of the first temperature detection unit 11. Thus, even if the heat capacities of the first temperature detection unit 11 and the pulsebeat measurement apparatus 1 become small as the pulsebeat measurement apparatus 1 is downsized, it is possible to absorb heat accumulated in the first temperature detection unit 11, thereby preventing the first temperature detection unit 11 from entering the thermal equilibrium state. Therefore, the pulsebeat measurement apparatus 1 can be downsized and operated stably.

Third Embodiment

A pulsebeat measurement apparatus 1 according to the third embodiment will be described. For example, consider a case in which a finger of a user is placed on a first temperature detection unit 11 and a second temperature detection unit 13 to measure the pulsebeat of the user. Each of the first temperature detection unit 11 and the second temperature detection unit 13 is an object having a rectangular shape with one side of about 1 mm to 2 mm, and is provided with a connecting portion that connects a resistance temperature detector and a lead wire by solder or the like. Therefore, a problem arises that when the finger of the user is placed on the first temperature detection unit 11 and the second temperature detection unit 13, the finger unwantedly contacts the connecting portion to prevent the finger from contacting the resistance temperature detector of each of the first temperature detection unit 11 and the second temperature detection unit 13 sufficiently, and each of the first temperature detection unit 11 and the second temperature detection unit 13 cannot detect the body temperature correctly. To solve this problem, the pulsebeat measurement apparatus 1 according to the third embodiment is different from the first embodiment in that the pulsebeat measurement apparatus 1 further includes a contact unit 18 which contacts the human body, and each of the first temperature detection unit 11 and the second temperature detection unit 13 detects the temperature of the human body via the contact unit 18.

Figure 8:
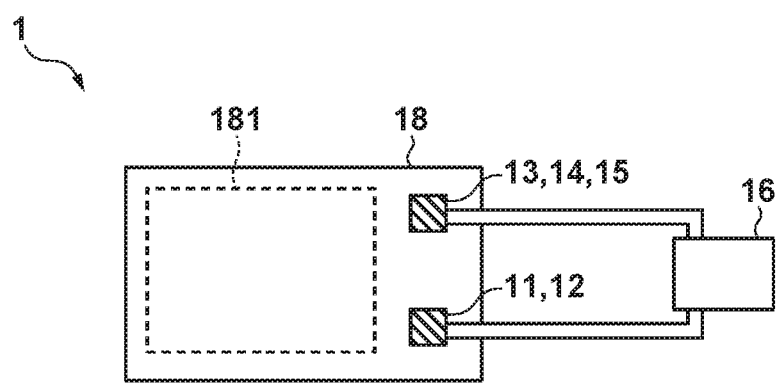
FIG. 8 is an example of a plan view showing a pulsebeat measurement apparatus according to an embodiment.

FIG. 8 is an example of a plan view showing the pulsebeat measurement apparatus 1 according to this embodiment. As shown in FIG. 8, the pulsebeat measurement apparatus 1 further includes the contact unit 18. The contact unit 18 is, for example, a metal plate with high heat conductivity or the like, and includes a contact region 181 to contact the human body (for example, the finger of the user for measuring the pulsebeat). The first temperature detection unit 11 and the second temperature detection unit 13 are connected to an end portion of the contact unit 18. An area of the contact unit 18 that can contact the human body is larger than an area of the resistance temperature detector of each of the first temperature detection unit 11 and the second temperature detection unit 13 that can contact the human body.

If the human body contacts the contact unit 18, each of the first temperature detection unit 11 and the second temperature detection unit 13 detects the temperature of the human body based on heat supplied from the human body via the contact unit 18. Thus, each of the first temperature detection unit 11 and the second temperature detection unit 13 can accurately detect the temperature of the human body via the contact unit 18 that has a relatively large contact area to readily contact the human body.

The present invention has been described above using the embodiments. However, the present invention is not limited to the technical scope described in the embodiments. Various modifications or improvements can be made for the embodiments, as is apparent to those skilled in the art. In particular, a detailed embodiment of distribution/integration of devices is not limited to that illustrated, and all or some of the devices can be functionally or physically distributed/integrated in an arbitrary unit in accordance with various additions or a functional load.

The invention claimed is:

1. A pulsebeat measurement apparatus comprising:
a first temperature detector configured to detect a temperature of a human body by contacting the human body;
a second temperature detector, having the same characteristic as that of the first temperature detector, configured to detect a temperature of the human body by contacting the human body;
a heat accumulator, contacting the second temperature detector, configured to suppress a change in temperature of the second temperature detector;
a specifying unit configured to specify a period of a change in temperature caused by a pulsation of the human body based on a difference between the temperature of the human body detected by the first temperature detector and the temperature of the human body detected by the second temperature detector; and
a pulsebeat measurement unit configured to measure a pulsebeat based on the specified period of the change in temperature.

2. The pulsebeat measurement apparatus according to claim 1, further comprising a heat insulator configured to suppress heat dissipation from the second temperature detector.

3. The pulsebeat measurement apparatus according to claim 2, wherein
the second temperature detector and the heat insulator are stacked, and
the heat accumulator is arranged to surround the second temperature detector in a direction orthogonal to a stacking direction of the second temperature detector and the heat insulator.

4. The pulsebeat measurement apparatus according claim 1, further comprising a contact unit contacting the human body and connected to the first temperature detector and the second temperature detector,
wherein each of the first temperature detector and the second temperature detector detects the temperature of the human body based on heat supplied from the human body via the contact unit.

5. The pulsebeat measurement apparatus according to claim 1, further comprising a heat absorber configured to absorb heat of the first temperature detector.

6. The pulsebeat measurement apparatus according to claim 5, wherein the heat absorber includes a Peltier device.

7. The pulsebeat measurement apparatus according to claim 1, wherein the specifying unit is further configured to specify the period of the change in temperature based on a moving average of the differences.

8. The pulsebeat measurement apparatus according to claim 1, wherein the specifying unit is further configured to specify the period of the change in temperature based on the difference obtained by applying a low-pass filter.

\* \* \* \* \*